(12) United States Patent
Weinstock

(10) Patent No.: US 12,151,235 B2
(45) Date of Patent: Nov. 26, 2024

(54) SEPARATOR AND METHOD FOR SEPARATING BLOOD PLASMA FROM BLOOD CELLS

(71) Applicant: Sarstedt AG & Co. KG, Nümbrecht (DE)

(72) Inventor: Mark Weinstock, Helmenzen (DE)

(73) Assignee: Sarstedt AG & Co. KG, Nümbrecht (DE)

( * ) Notice: Subject to any disclaimer, the term of this patent is extended or adjusted under 35 U.S.C. 154(b) by 1101 days.

(21) Appl. No.: 16/988,772

(22) Filed: Aug. 10, 2020

(65) Prior Publication Data

US 2021/0046402 A1 Feb. 18, 2021

(30) Foreign Application Priority Data

Aug. 13, 2019 (DE) ..................... 10 2019 121 723.7

(51) Int. Cl.
*B01L 3/00* (2006.01)
*B29C 45/00* (2006.01)
*G01N 33/49* (2006.01)

(52) U.S. Cl.
CPC ......... *B01L 3/50215* (2013.01); *B01L 3/5082* (2013.01); *B29C 45/0017* (2013.01); *B01L 2200/0689* (2013.01); *B01L 2200/12* (2013.01); *B01L 2400/0605* (2013.01); *G01N 33/491* (2013.01)

(58) Field of Classification Search
CPC ............... B01L 3/50215; B01L 3/5082; B01L 2200/0689; B01L 2200/12; B01L 2400/0605; B29C 45/0017; G01N 33/491; G01N 33/48; A61M 39/24
See application file for complete search history.

(56) References Cited

U.S. PATENT DOCUMENTS

| 3,887,464 A | 6/1975 | Ayres |
| 4,027,660 A * | 6/1977 | Wardlaw ............. B01L 3/50215 422/918 |
| 4,818,386 A | 4/1989 | Burns |

(Continued)

FOREIGN PATENT DOCUMENTS

| CN | 1206832 A | 2/1999 |
| CN | 1426761 A | 7/2003 |

(Continued)

OTHER PUBLICATIONS

Holden et. al. "Thermoplastic Elastomers". J. Polymer Sci: Part C No. 26, pp. 37-57 (Year: 1969).*

*Primary Examiner* — Liam Royce
(74) *Attorney, Agent, or Firm* — Smartpat PLC

(57) ABSTRACT

The invention relates to a separator for separating blood plasma and blood cells in a blood collection tube. The separator comprises a float with a first density and at least one passage opening. In addition to the float, the separator comprises a ballast with a second density that is greater than the first density. The total density of the separator, that is, the float and the ballast together, lies between the density of the plasma and the density of the cells in the blood. The float forms a valve together with the ballast. The float and the ballast are arranged so as to be movable relative to each other. In accordance with the invention, the ballast has at least one valve element for opening or closing a passage opening in the float.

19 Claims, 5 Drawing Sheets

(56) References Cited

U.S. PATENT DOCUMENTS

| | | |
|---|---|---|
| 6,479,298 B1 | 11/2002 | Miller et al. |
| 7,188,734 B2 | 3/2007 | Konrad |
| 7,374,678 B2 * | 5/2008 | Leach ................. B01L 3/50215 494/67 |
| 2002/0094305 A1 | 7/2002 | DiCesare et al. |
| 2003/0069519 A1 | 4/2003 | Sarstedt |
| 2005/0059163 A1 | 3/2005 | Dastane et al. |
| 2010/0155319 A1 | 6/2010 | Felix et al. |
| 2010/0288694 A1 | 11/2010 | Crawford et al. |
| 2013/0017130 A1 | 1/2013 | Haubert |
| 2013/0140226 A1 | 6/2013 | Lundquist et al. |
| 2013/0164195 A1 | 6/2013 | Felix et al. |
| 2013/0315798 A1 | 11/2013 | Crawford et al. |
| 2014/0057770 A1 | 2/2014 | Holmes et al. |
| 2016/0008808 A1 * | 1/2016 | Levine ................. B01L 3/0282 422/522 |
| 2017/0304823 A1 | 10/2017 | Sparks et al. |
| 2021/0283599 A1 | 9/2021 | Weinstock et al. |

FOREIGN PATENT DOCUMENTS

| | | |
|---|---|---|
| CN | 103200976 A | 7/2013 |
| CN | 102458661 B | 11/2015 |
| CN | 107051758 A | 8/2017 |
| CN | 207908244 U | 9/2018 |
| CN | 109395895 A | 3/2019 |
| DE | 2819170 A1 | 11/1978 |
| DE | 102017108935 | 12/2018 |
| EP | 0311011 A2 | 4/1989 |
| EP | 0311011 B1 | 6/1993 |
| EP | 1006360 A2 | 6/2000 |
| JP | H10369069 U | 7/1991 |
| JP | 2011528802 A | 11/2011 |
| JP | 2012510853 A | 5/2012 |
| JP | 2012526994 A | 11/2012 |
| JP | 2019101046 | 2/2020 |
| WO | 2010065018 A1 | 6/2010 |
| WO | 2011069145 A2 | 6/2011 |
| WO | 2011126868 A1 | 10/2011 |

* cited by examiner

SEPARATOR AND METHOD FOR SEPARATING BLOOD PLASMA FROM BLOOD CELLS

TECHNICAL FIELD

The disclosure relates to a separator along with a method for separating blood cells and blood plasma in a blood collection tube. The disclosure further relates to a blood collection tube with said separator and to a method for manufacturing the separator.

BACKGROUND

Separators for blood collection tubes along with corresponding blood collection tubes are generally known, for example from the international patent application WO 2010/132783 A1 or from European patent EP 0311011 B1. The separators disclosed therein consist of a float with a first density and at least one passage opening along with a ballast with a second density that is greater than the first density of the float. The total density of the separator, that is the float and the ballast together, lies between the density of the plasma and the cells in the blood. The float and the ballast in accordance with EP patent EP 0311011 B1 are designed to be movable relative to each other and together form a valve. To realize a valve function in the separator, the float and the ballast are each designed with bead-like edges. To open the valve for a liquid, for example blood, the opposing bead-like edges of the float and the ballast move away from each other and are spaced apart from each other; to close the valve, the bead-like edges move towards each other and then lie against each other in a sealing manner. On its underside turned towards the passage opening in the float, the ballast has at least one groove or at least one channel, as the case may be, in order to ensure that the liquid can pass through the passage opening even if the underside of the ballast is pressing against the float, for example due to the action of a centrifugal force.

The technical teaching of EP 0 311 011 B1 has the following disadvantages: The ability to produce this technical teaching seems to be possible only with great effort. Only manual assembly of the components after the provision of the corresponding individual parts seems to be possible. Furthermore, the formation of the bead-like edges on both the float and the ballast is complex and relatively expensive. The exchange of liquid through the narrow gaps between the edges increases the risk of hemolysis and possibly a longer separation time. Hemolysis in particular leads to the contamination of the blood plasma that is to be obtained during separation. Finally, the functionality seems highly theoretical. In particular the approach that the different pressures within the shown chambers have an influence on the valve position is most likely accompanied by filling problems, long filling times and possibly also problems with the concentration of the preparation. Specifically, cell deposition in the flat area of the ballast of EP0311011 B1 leads to poorer sample quality.

SUMMARY

The disclosure is based on the object of providing an alternative separator for a blood collection tube, a blood collection tube with the alternative separator, an alternative method for separating blood cells and blood plasma, along with an alternative method for manufacturing the separator.

This object is achieved with the separator as disclosed. Accordingly, the ballast for the formation of the valve further has at least one valve member for opening or closing the passage opening in the float.

The term "passage opening" means a hole or through-bore in the float for the passage of a liquid from one side of the float to the opposite side of the float. The passage opening is designed to be large enough so that, when open, it allows easy exchange of the liquid between the chambers above and below the separator in the blood collection tube. In this manner, the risk of hemolysis and possibly a longer separation time are reduced.

The terms "top, above, bottom, below, vertical and horizontal" refer to the orientation of the separator in space as shown in particular in FIG. 1.

Given that the ballast of the separator is located below the float, the valve opens while the separator moves from its initial position to the phase boundary between the blood plasma and the blood cells due to the action of centrifugal force. During this time, it is possible that air bubbles, which are initially present in the blood collection tube below the separator, can still pass through the opened passage opening into the upper part of the collected blood in the blood collection tube, that is, into the plasma, until the passage opening is closed, and from there escape into the area above the phase boundary. In addition, the air bubbles can also rise up between the sealing edge and the wall of the sample tube from the area below the separator into the area above the separator due to a highly elastic sealing edge of the float. Both possibilities offer the advantage that buoyancy of the air bubbles below the separator does not prevent the separator from sinking to the phase boundary. In addition, an inclined arrangement of the separator within the blood collection tube in the boundary layer is avoided in this manner. Instead, the separator in the boundary layer aligns itself straight, that is, symmetrically to the longitudinal axis of the blood collection tube.

The passage opening in the float is to be able to be opened or closed with the ballast as a function of the amount of centrifugal force acting on the ballast and the float. The interaction between the density of the liquid sample in the blood collection tube and the density of the float and the ballast causes the valve to open. For this purpose, a reset element for resiliently connecting the float to the ballast is provided in such a manner that opening the valve requires a force to overcome a restoring force defined by the reset element. Upon the intended use of the separator, namely for separating plasma or serum, as the case may be, and cells in blood, the force required is applied by action of the centrifugal forces.

The float is advantageously designed in the form of a funnel in accordance with another exemplary embodiment. This design of the separator offers—depending on the steepness of the funnel opening—the advantage that only very few cells, ideally no cells, from the blood additionally adhere to the surface of the float. Instead, under the influence of centrifugal force, preferably all cells migrate through the passage opening in the float into the area below the separator in the blood collection tube. In this manner, the quality of the liquid or blood sample, as the case may be, to be analyzed later, which in particular consists of the liquid above the separator, is significantly improved. The ballast is located below the float, in particular outside the funnel.

The passage opening in the float is preferably aligned such that the perpendicular to the plane it spans coincides with the major axis of the separator, that is, the angle between the specified perpendicular and the major axis of the separator amounts to 0°. However, this is not a mandatory design: Rather, in principle, there can be any angle between the perpendicular and the main axis; the only requirement is that the passage opening in the float can be closed by the ballast. In this respect, the claimed angles of α=±45° or α=±10°, as the case may be, are to be understood only as examples and in no way as singular limitations. Additional designs of the separator, in particular concerning the design of the valve member on the ballast for closing the passage opening in the float, the design of the reset element, the design of the funnel, concerning the material of the float and concerning the mounting of the ballast on the float, comprise the subject matter of the dependent claims for the claimed separator.

The aforementioned object is achieved by a blood collection tube with the described separator. This is characterized in that the maximum outer diameter of the float formed by the circumferential sealing edge is larger than the inner diameter of the blood collection tube for a circumferential sealing contact of the sealing edge with the inner sides of the walls of the blood collection tube.

The aforementioned object is further achieved by a method as claimed. The advantages of such method correspond to the advantages mentioned above with regard to the separator. According to the method, the separator, after its release from the initial position A—overcoming the static friction between the sealing edge of the separator and the inner walls of the blood collection tube by centrifugal force—migrates into the boundary layer between the plasma and the cells of the separated blood. After the axial alignment of the separator, its circumferential sealing edge is in full sealing contact with the inner side of the blood collection tube. The alignment of the valve in the vertical direction requires the start of centrifugation. When an increasing centrifugal force is applied to the separator, it sinks in the direction of the phase boundary between the components of the liquid to be separated, in the case of blood between the plasma and the blood cells. After the axial alignment of the separator in the boundary layer, the valve is closed again after the centrifugal force has ceased due to the restoring force of a reset element.

In this context, the term "axial alignment" means that the separator within the blood collection tube is arranged in the boundary layer in such a manner that its main axis ideally coincides with the longitudinal axis of the blood collection tube. Minor angular deviations between the main axis and the longitudinal axis are included in the term "axial alignment"; however, the prerequisite is in any case that, even if the separator is inclined, the circumferential sealing edge of the float must still be in circumferential sealing contact with the inner sides of the walls of the blood collection tube.

The terms "phase boundary" and "boundary layer" are used synonymously. Both terms mean the transition between the liquid components of different densities above and below the separator. The liquid components to be separated, for example blood cells and blood plasma, have different densities. The density of the separator is selected so that it lies between the densities of the two liquid components. This ensures that, upon the centrifugation of the blood collection tube with the liquid, the separator is placed/moved exactly between the two liquid components to be separated, that is, the phase boundary.

The term "main axis of the separator" means the axis in vertical direction through the float and the ballast, as shown in particular in FIG. 1.

The aforementioned object is finally also achieved by a method for manufacturing the separator. The two-component injection molding process is particularly suitable for manufacturing the separator, wherein the float forms one component and the ballast forms the other component. It is important that the two components are injection molded from different materials, which do not form any chemical or material bond with each other and do not have any adhesion to each other. This is important because the float and the ballast must remain movable completely independently of each other or relative to each other, as the case may be, without "sticking" to each other. In particular, this two-component injection molding process offers the advantage that manual assembly work is largely eliminated, and therefore the separator can be manufactured very economically and with relatively little effort. Alternatively, the float and the ballast can each be manufactured independently of one another, for example by means of injection molding, and then joined together. It is also possible to first manufacture the ballast, then place it in another injection mold and mold the float, such that the ballast is overmolded.

The following detailed description is merely exemplary in nature and is not intended to limit the invention or the application and uses of the invention. Furthermore, there is no intention to be bound by any theory presented in the preceding background or the following detailed description.

DETAILED DESCRIPTION

The invention is described in detail below with reference to the figures mentioned in the form of exemplary embodiments. In all figures, the same technical elements are designated with the same reference signs.

Figure 1:
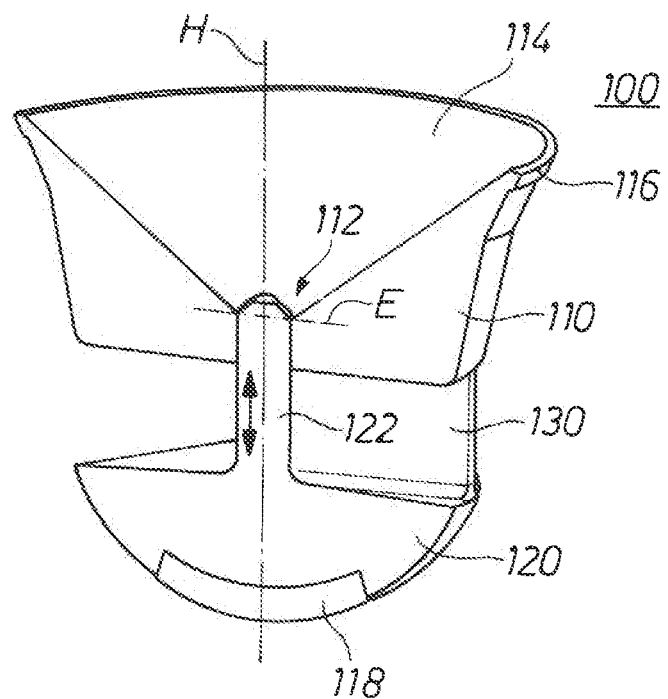
FIG. 1 shows a first exemplary embodiment for the separator.
Figure 9:
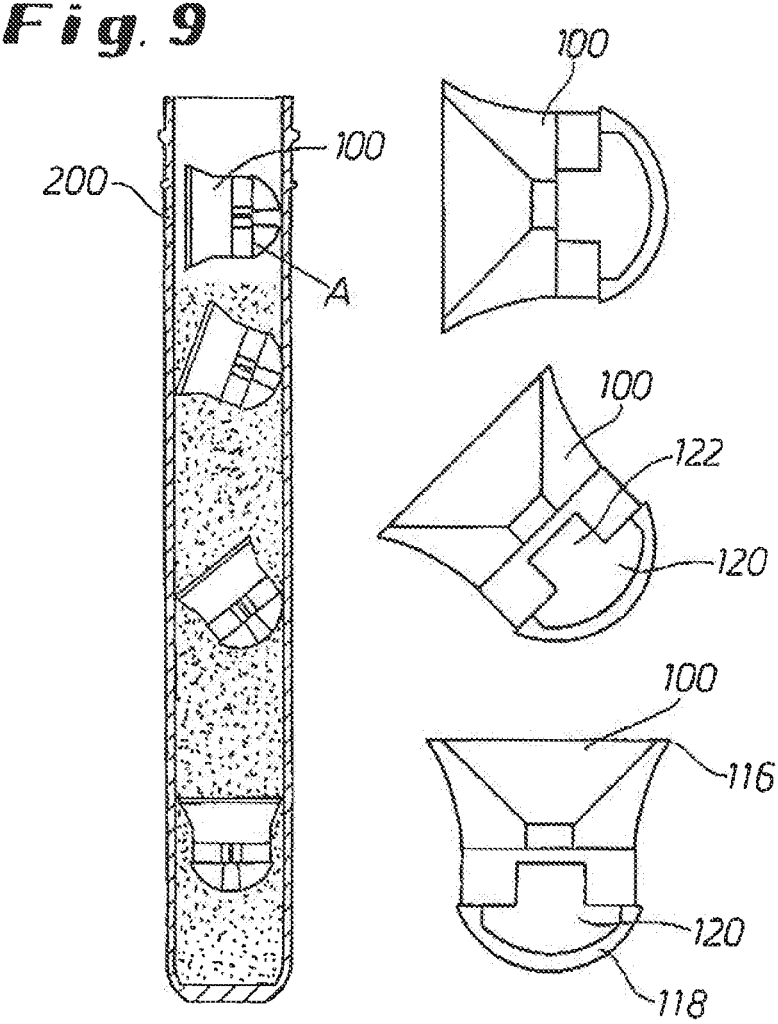
FIG. 9 shows the blood collection tube with the separator in different positions during centrifugation.

FIG. 1 shows the separator 100 for use in a blood collection tube 200; see, for example, FIG. 9. The blood collection tube is used to collect blood from a patient. The separator 100 in the blood collection tube is used to separate blood plasma and blood cells in the blood during the centrifugation of the blood collection tube. The specified centrifugation process is an essential component of the pre-analysis of blood for medical purposes. The separator 100 has a float 110 with a first density and at least one passage opening 112. At least one circumferential sealing edge 116 is formed on the float for a circumferential sealing contact with the inner side of the blood collection tube. In addition to the float, the separator 100 has a ballast 120 with a second density that is greater than the first density of the float 110. The total density of the separator, that is, the float and the ballast considered together, lies between the density of the plasma and the density of the cells in the blood.

The float 110 and the ballast 120 together form a valve for opening or closing the passage opening 112 in the float 110. For this purpose, the float 110 and the ballast 120 are arranged so as to be movable relative to each other in the direction of the double arrow.

The reset element 130 provides a resilient connection between the float 110 and the ballast 120 in such a manner that a force is required to open the valve, because a resetting force defined by the reset element 130 must be overcome. The reset element can be connected to the float and to the ballast. However, this is not necessary in the design shown in FIGS. 1 to 3; there, the elastic connection is realized by the fact that the reset element forms a resilient connection between the float and the retaining bracket 118 and the ballast 120 is supported by the retaining bracket 118. The reset element 130 can be made of the same material as the float 110 and optionally also of the same material as the retaining bracket 118; preferably, it is formed in one piece with the float and the retaining bracket 118. Alternatively, the reset element may also be made of the same material as the ballast and preferably in one piece with it.

Figure 6:
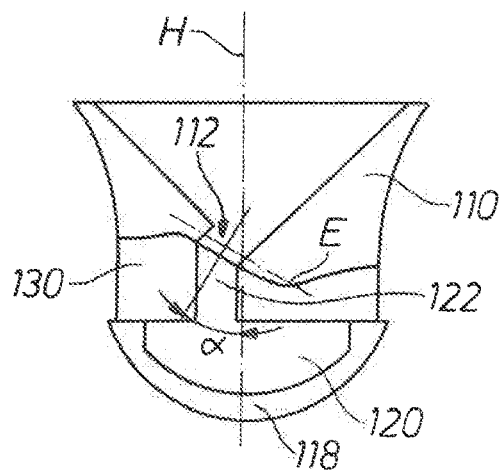
FIG. 6 shows a fourth exemplary embodiment for the separator in a cross-section.

To form the valve, the at least one passage opening 112 in the float 110 is opened in the direction of the ballast 120. With the exemplary embodiment shown in FIG. 1, the plane E spanned by the passage opening 112 is perpendicular to the main axis H of the separator 100. In other words, the perpendicular to the plane E coincides with the main axis H or is aligned parallel to the main axis H, as the case may be. However, such design of the passage opening 112 is by no means mandatory, as is also shown in FIG. 6 below.

In order to form the valve, it is further necessary that the ballast 120 has at least one valve member 122 for opening or closing the passage opening 112 in the float 110. The valve member in FIG. 1 is designed, for example, in the form of a pin 122, which can be inserted into the passage opening 112 in the float 110 in order to seal it.

The float 110 is preferably designed in the form of a funnel. The funnel tapers from an upper passage opening cross-section 114 towards the at least one passage opening 112 and opens into such passage opening 112. The circumferential sealing edge 116 on the upper passage opening cross-section 114 may be designed for a circumferential sealing contact with the inner sides of the walls of the blood collection tube 200. The upper large passage opening cross-section 114 is arranged above the passage opening 112 in relation to the vertical orientation of the separator, as shown in FIG. 1.

Figure 2:
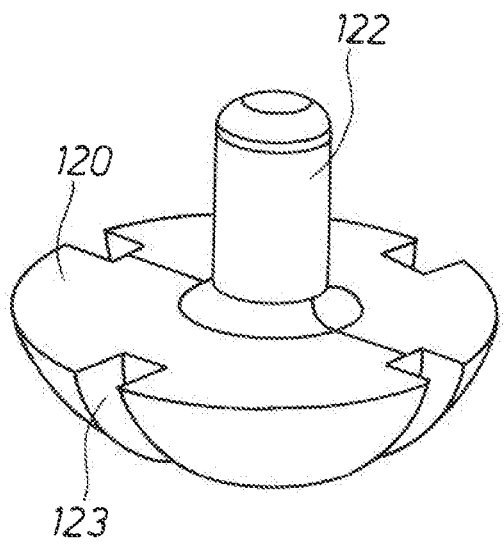
FIG. 2 shows the ballast of the separator according to FIG. 1 as a single part.

FIG. 2 shows the ballast 120 with the specified pin 122 in a single representation.

Figure 3:
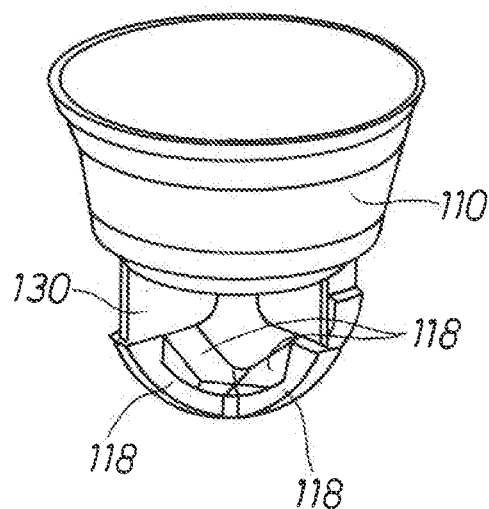
FIG. 3 shows the float of the separator according to FIG. 1 as a single part.

FIG. 3 shows the float 110, as it is also shown in FIG. 1, in a single representation. It can be seen that reset elements 130 are arranged on the underside of the float, which carry retaining brackets 118 that serve to receive and hold the ballast 120. The float 110, the reset elements 130 and the retaining brackets 118 can be made of the same material and are preferably also formed in one piece. The grooves 123 recognizably formed in FIG. 2 at the edge of the ballast 120 serve to receive the retaining bracket 118 shown in FIG. 3. When assembled, the ballast 120 according to FIG. 2 and the float 110 with the restoring element 130 and the retaining bracket 118 according to FIG. 3 form the separator 100 shown in FIG. 1.

Figure 4:
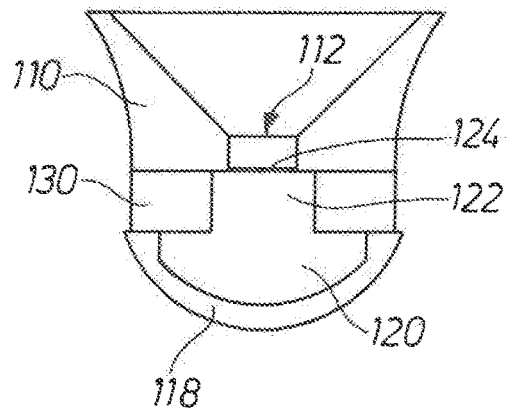
FIG. 4 shows a second exemplary embodiment for the separator in a cross-section.

FIG. 4 shows a second exemplary embodiment for the separator 100 in a cross-section, wherein such exemplary embodiment is characterized in that the pin 122 of the ballast 120 here is designed to be larger than the passage opening cross-section of the passage opening 112, such that the pin 122 cannot penetrate into the passage opening 112. In this exemplary embodiment, the closing of the passage opening 112 is realized in that the closing element 124 is designed in the form of a contact surface as a surface area on the front side of the pin 122. The contact surface covers the passage opening 112 in the float in a sealing manner.

Figure 5:
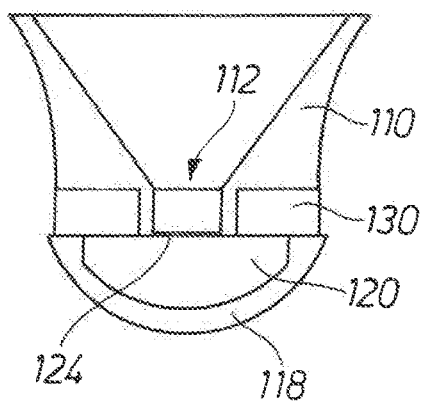
FIG. 5 shows a third exemplary embodiment for the separator in a cross-section.

FIG. 5 shows a third exemplary embodiment of the separator 100. With this design, the passage opening 112 of the float 110 opens into a short channel directed towards the ballast. The end of the channel on the ballast side, and thus the passage opening 112, is here also covered in a sealing manner and thus closed by a contact surface 124 as a surface area on the ballast 120. In this exemplary embodiment, a pin 122 on the ballast 120 is not required.

FIG. 6 shows a fourth exemplary embodiment for the separator, with which the passage opening 112 is inclined at an angle α with respect to the main axis H of the separator. The plane E spanned by the passage opening 112 forms with its perpendicular the angle α to the main axis H. In this case, as in all other exemplary embodiments, it is important that the ballast or its valve member, as the case may be, is designed in such a manner that, in this case as well, it covers the passage opening 112 in a sealing manner. With the fifth exemplary embodiment shown in FIG. 6, this can be achieved by chamfering the upper end face of the pin 122 in accordance with the passage opening 112 and by providing an additional sealing contact surface. In principle, the angle α can assume any value between 0°≤α<90°; however, it preferably amounts to 0°.

Figure 7:
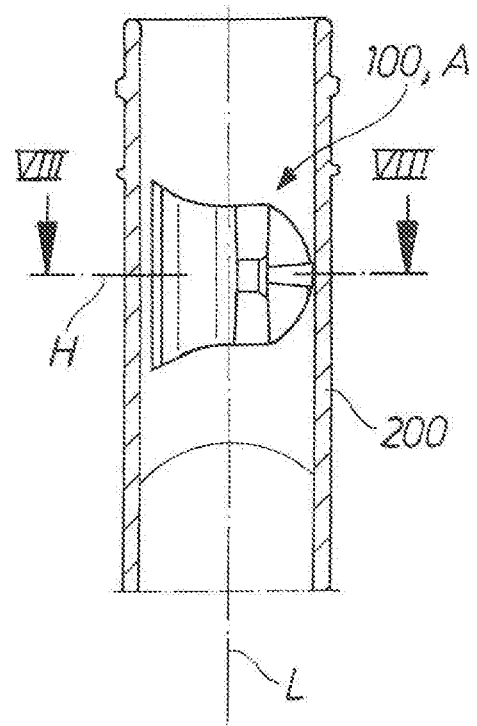
FIG. 7 shows a blood collection tube in a cross-sectional view with the separator in an initial position.

In the following, the method for separating blood into plasma and cells in a blood collection tube 200 with the assistance of the separator is described in more detail:

FIG. 7 shows the blood collection tube 200 with the separator 100 arranged therein in a delivery state or an initial state or in an initial position A, as the case may be. Thereby, the blood collection tube is closed with a screw cap. In the delivery state A, the separator is rotated by approximately 90° to the longitudinal axis L of the blood collection tube. This ensures that a blood sample taken can flow past the separator 100 into the lower part of the blood collection tube. Thereby, the valve inside the separator 100 is in the closed position (FIG. 7).

The blood collection tube is filled with blood via its closure cap, for example a screw cap.

Figure 8:
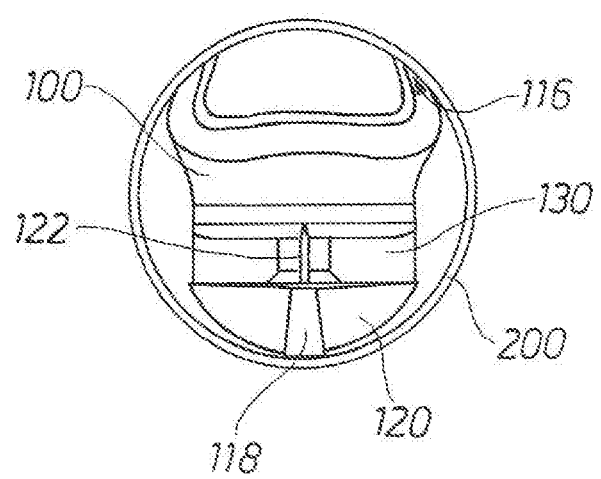
FIG. 8 shows the separator in the initial position according to FIG. 7 in a plan view.

FIG. 8 shows the separator 100 positioned in its initial position A inside the blood collection tube 200 in a top view. In this position, the sealing edge 116 is compulsorily severely deformed; as such, it is important that the float is made of elastic material.

In this initial position A, the blood flows past the separator or the inner wall of the blood collection tube. Thereby, as mentioned before, the valve is closed, such that no blood can flow through the separator.

FIG. 9 shows a cross-section through the blood collection tube 200 with the separator in various locations or positions, as the case may be, under the influence of centrifugation.

The blood collection tube is centrifuged in order to centrifuge the blood collected from a patient and in this manner separate it into the specified blood plasma and cells. During centrifugation, the separator 100 swings out of its initial position A. Due to the ever increasing centrifugal force on the separator and the elastic connection of the ballast 120 to the float 110, the valve opens, such that it is now also possible to exchange fluid through the separator 100. Specifically, the cells in the blood migrate due to the centrifugal force through the passage opening 112 in the separator 100 into the lower part of the blood collection tube, because the cells are heavier than the blood plasma. The blood plasma does not pass through the passage opening 112, but instead remains in the upper part of the blood collection tube above the separator 100. Centrifugation moves the separator 100 in the blood collection tube to the level, that is, the height range of the phase boundary between the heavier cells and the lighter blood plasma, in order to separate these two components from each other. If the separator 100 is in this phase boundary, also called boundary layer G, the sealing edge 116 is in circumferential sealing contact with the inner sides of the walls of the blood collection tube, because its diameter in the relaxed state is larger than the inner diameter of the blood collection tube.

Figure 10:
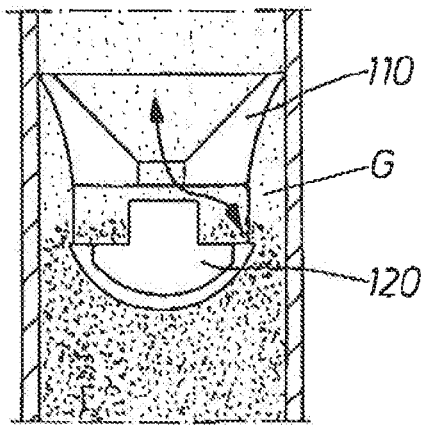
FIG. 10 shows the separator in the blood collection tube in the end position in a boundary layer between blood plasma and blood cells with the valve still open.
Figure 11:
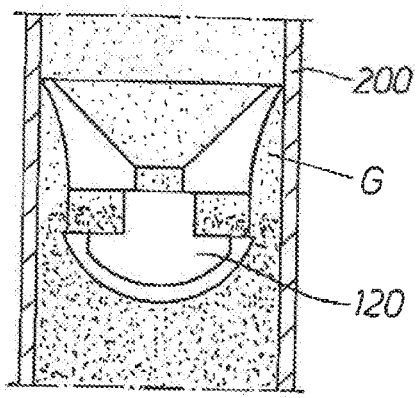
FIG. 11 shows the separator in the end position according to FIG. 10, but this time with the valve closed.

In the phase boundary or boundary layer G, as the case may be, the valve or the passage opening 112, as the case may be, in the float 110 is initially still open in accordance with FIG. 10. As long as centrifugation continues, the open valve enables cavity communication, that is, a barrier-free exchange of individual components of the blood between the area above and below the separator 100 in the blood collection tube and thus the specified phase separation. Once the phase separation is complete, the centrifugation stops. The lack of centrifugal force then causes the ballast to move towards the float 110 due to the restoring force exerted by the reset element 130 and the passageway 112 is closed; see FIG. 11. The upper and lower cavities, that is, the area above and below the separator 100 in the blood collection tube, are now tightly separated by the fit of the sealing lip 116 to the inner sides of the walls of the blood collection tube and by the closed valve in the separator. This also effectively separates the blood plasma and cells from each other, as desired.

Figure 12:
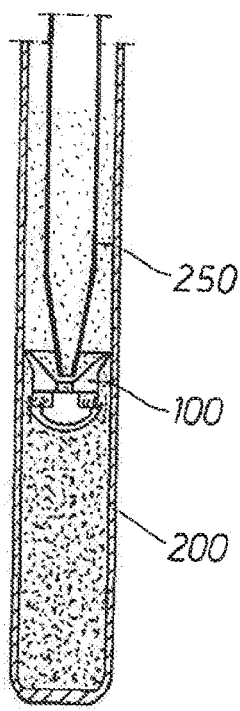
FIG. 12 shows a first option for withdrawing blood plasma from the blood collection tube after centrifugation.

The blood plasma, which is particularly important for blood analysis, can now be pipetted off with the assistance of a pipette tip 250, as shown in FIG. 12. Here, the funnel-shaped design of the float offers the particular advantage that the pipette tip can protrude into the area of the passage opening 112 and can thus also remove the last remaining residue of blood plasma from the upper cavity.

Figure 13:
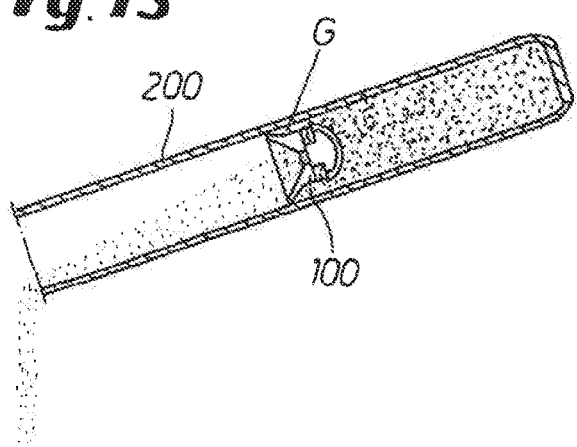
FIG. 13 shows a second option for withdrawing the blood plasma from the blood collection tube after centrifugation.

Finally, FIG. 13 shows the possibility of draining the blood plasma by tilting the blood collection tube; this is made possible in particular by the fully sealing fit of the separator 100 with its sealing lips 116 inside the blood collection tube and the closed valve.

Throughout this specification and the following claims, the indefinite article "a" or "an" does not exclude the possibility that more than one of the element is present, unless the context clearly requires that there is one and only one of the elements. The indefinite article "a" or "an" thus usually means "at least one". The coordinating conjunction "or" is not used to express exclusivity. A reference to "A or B" being present is true if A alone is present, B alone is present, or both A and B are present.

While the present invention has been described with reference to exemplary embodiments, it will be readily apparent to those skilled in the art that the invention is not limited to the disclosed or illustrated embodiments but, on the contrary, is intended to cover numerous other modifications, substitutions, variations and broad equivalent arrangements that are included within the spirit and scope of the following claims.

LIST OF REFERENCE SIGNS

100 Separator
110 Float
112 Passage opening in the float
114 Passage opening cross-section
116 Sealing edge
118 Retaining bracket
120 Ballast
122 Valve member, for example pin
123 Grooves in the ballast
124 Valve member
130 Reset element
200 Blood collection tube
250 Pipette tip
d Inner diameter of the blood collection tube
A Initial position
E Plane spanned by the passage opening
G Boundary layer
H Main axis of the separator
L Longitudinal axis of the blood collection tube
α Angle

What is claimed is:

1. A separator for separating blood plasma and blood cells in a blood collection tube, comprising:
   a float having a first density and a passage opening; and
   a ballast having a second density that is greater than the first density;
   wherein the passage opening is a hole or bore through which liquid can flow from a chamber above the separator to a chamber below the separator,
   wherein a total density of the float and the ballast is between a density of the plasma and a density of the cells in the blood;
   wherein the float and the ballast are movable relative to each other and together form a valve; and
   wherein the ballast includes a valve member for opening or closing the passage opening in the float.

2. The separator according to claim 1,
   wherein the valve member has the form of a pin, which is configured to be inserted into the passage opening in the float.

3. The separator according to claim 1,
   wherein the valve member a contact surface on the ballast for covering the passage opening in the float in a sealing manner.

4. The separator according to claim 1,
   further comprising a reset element which provides a resilient connection between the float and the ballast,
   wherein a force is required to open the valve and overcome a restoring force defined by the reset element.

5. The separator according to claim 4,
   wherein the reset element is made from the same material as the float.

6. The separator according to claim 4,
   wherein the reset element and the float are one piece.

7. The separator according to claim 4,
   wherein the reset element is made from the same material as the ballast.

8. The separator according to claim 4,
   wherein the reset element and the ballast are one piece.

9. The separator according to claim 1,
wherein the float is shaped as a funnel,
wherein the funnel tapers towards the passage opening and opens into the passage opening, starting from a passage opening cross-section, on which a circumferential sealing edge is formed for a circumferential sealing contact with an inner side of a wall of the blood collection tube, and
wherein the passage opening cross-section is arranged above the passage opening.

10. The separator according to claim 1,
wherein the float is made of an elastic material.

11. The separator according to claim 1,
wherein the passage opening is aligned in such a manner that a perpendicular to a plane spanned by the passage opening has an angle ($\alpha$) between 45° and 0° relative to a main axis of the separator.

12. The separator according to claim 1,
wherein the float has at least one retaining bracket for holding or guiding the ballast.

13. A blood collection tube, comprising:
the separator according to claim 9,
wherein a maximum outer diameter the circumferential sealing edge of the float is larger than an inner diameter of the blood collection tube for a circumferential sealing contact with an inner side of a wall of the blood collection tube.

14. A method for separating blood into plasma and cells, comprising:
providing a blood collection tube with the separator according to claim 1 therein arranged in an initial position in a transverse orientation;
introducing blood into the tube, wherein the blood flows past an outside of the separator in the transverse orientation into an interior of the tube;
centrifuging the tube with the blood contained therein, wherein the blood plasma and blood cells separate, and wherein the separator separates from the initial position, changes into an axial alignment with a longitudinal axis of the blood collection tube and migrates into a boundary layer between the separated plasma and the cells;
wherein the valve is closed in the separator in the initial position; and
wherein the valve opens under the action of centrifugal force against a restoring force, such that the heavier cells of the blood compared to the plasma pass through the opened passage opening in the float under the action of centrifugal force during centrifugation and accumulate in the blood collection tube below the separator, while the lighter plasma remains in the blood collection tube above the separator.

15. The method according to claim 14,
wherein the separator, after its release from the initial position, migrates into the boundary layer while overcoming static friction by the centrifugal force, and
wherein a circumferential sealing edge of the separator, after the axial alignment of the separator with the valve, bears against an inner side of the blood collection tube in a frictionally locking and fully sealing manner, and
wherein after its axial alignment in the boundary layer and after the centrifugal force has ceased the valve closes again due to an acting restoring force.

16. The method according to claim 15,
wherein following the axial alignment of the separator in the boundary layer and after closing the valve, the plasma is removed from the blood collection tube by pipetting off with a pipette or by tilting.

17. The method according to claim 14,
wherein the separator in the transverse orientation is aligned with its main axis transverse to the longitudinal direction of the blood collection tube.

18. A method, comprising:
manufacturing the separator according to claim 1 by a two-component injection molding process,
wherein the float is a first component and the ballast is a second component without forming a bonded connection between the float and the ballast, or
wherein the float and the ballast are each manufactured independently of one another by of injection molding and then joined together.

19. The separator according to claim 1,
wherein the valve member has the form of a pin.

* * * * *